United States Patent [19]

Gober

[11] Patent Number: 5,052,398
[45] Date of Patent: Oct. 1, 1991

[54] QRS FILTER FOR REAL TIME HEART IMAGING WITH ECG MONITORING IN THE MAGNETIC FIELD OF AN NMR IMAGING SYSTEM AND NMR IMAGING APPARATUS EMPLOYING SUCH FILTER

[75] Inventor: Joel R. Gober, San Pedro, Calif.

[73] Assignee: North American Philips Corporation, New York, N.Y.

[21] Appl. No.: 548,345

[22] Filed: Jun. 29, 1990

[51] Int. Cl.$^5$ .............................................. A61B 5/04
[52] U.S. Cl. ................... 128/696; 128/653 X
[58] Field of Search ................ 128/653 X, 696, 708

[56] References Cited

U.S. PATENT DOCUMENTS

| | | | |
|---|---|---|---|
| 3,654,916 | 4/1972 | Neilson | 128/702 |
| 4,237,903 | 12/1980 | Hofmann | 128/708 |
| 4,494,551 | 1/1985 | Little, III et al. | 128/696 |
| 4,694,837 | 9/1987 | Blakeley et al. | 128/696 |
| 4,708,144 | 11/1987 | Hamilton | 128/208 |
| 4,887,609 | 12/1989 | Cole, Jr. | 128/696 |
| 4,895,157 | 1/1990 | Nambo | 128/696 |

OTHER PUBLICATIONS

Thakor, Webster, & Thompkins, "Estimation of QRS Complex Power Spectra for Design of a QRS Filter", IEEE Transactions on Biomedical Engineering, vol. BME-31, No. 11, Nov. 1984, pp. 702-706.

De Vel, "R-Wave Detection in the Presence of Muscle Artifacts", IEEE Transactions on BioMedical Engineering, vol. BME-31, No. 11, Nov. 1984, pp. 715-717.

Primary Examiner—William E. Kamm
Attorney, Agent, or Firm—William Squire

[57] ABSTRACT

A pair of Butterworth 4th order filters are cascaded with an absolute value filter to filter the QRS wave of an ECG signal generated in a magnetic field of an NMR imaging system. The NMR system includes a magnet for producing a static $B_O$ field and a set of coils for producing RF pulse induced fields in which an ECG monitoring system is located. The ECG monitoring system transmits the resultant QRS waves to a receiver which processes the received signals and applies the received signals to a display via the above filters. The $-3$ dB point of the high pass filter is at about 10 Hertz to filter the T-wave and Bo field induced breathing artifacts and the $-3$ dB point of the low pass filter is about 20 Hertz to filter the high frequency components of pulsed static field gradient noise created by the NMR system.

15 Claims, 2 Drawing Sheets

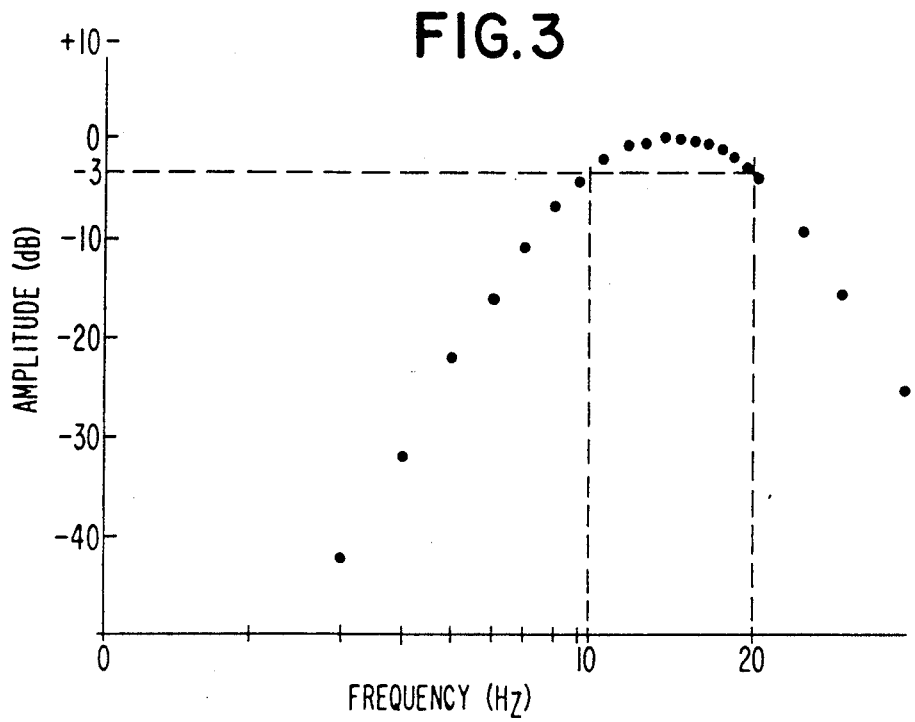
FIG. 4b
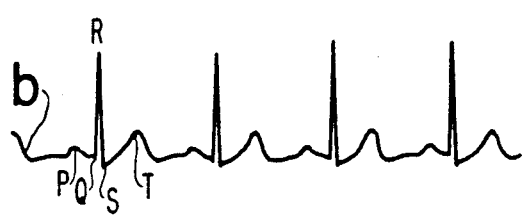
FIG. 4a

QRS FILTER FOR REAL TIME HEART IMAGING WITH ECG MONITORING IN THE MAGNETIC FIELD OF AN NMR IMAGING SYSTEM AND NMR IMAGING APPARATUS EMPLOYING SUCH FILTER

BACKGROUND OF THE INVENTION

1. Field of the Invention

The present invention relates to QRS wave filters for use in a heart monitoring ECG system, and particularly, for use in an NMR imaging system.

2. Description of the Prior Art

QRS wave filters are known. A QRS wave is an important component of the electrical activity of the heart and corresponds to end diastole. For example, an article by Thakor et al. "Estimation of QRS Complex Power Spectra for Design of a QRS Filter" IEEE Transactions on Biomedical Engineering, Vol. BME-31, No. 11, November 1984, pages 702-706, discusses filtering ECG waveforms presenting spectral analysis of ECG waveforms. They indicate that the QRS complex can be separated from other interfering signals. They disclose that a bandpass filter would be of use in many ECG monitoring instruments. A particular filter is disclosed. Disclosed as interference are noise signals due to motion artifacts, muscles and 60 Hz powerline noise. However, this filter is not particularly useful in a Nuclear Magnetic Resonance imaging (NMR) system.

In an NMR system the ECG monitoring probes and wires need be placed on the chest of a patient. Such wires move about due to the breathing of the patient. The present inventor recognizes a need for an ECG filter which will filter breathing induced noise on the wires in the presence of a static magnetic (Bo) field. There is no recognition in the Thakor et al. article of the nature of such noise in which the motion of the wires in the Bo field cause currents, i.e., noise, to be induced in the ECG wires. Further, another problem recognized by the present inventor is that it would be desirable to provide an ECG signal in real time with an image of the heart. In this way a pathological malfunction can be visually observed on a monitor simultaneously with the QRS Wave. Timing is extremely important for the QRS wave and image to enhance correct diagnosis of the pathology. The Thakor article bandpass filter also does not allow for such timing and does not address the problem of such a delay in the filtered signal which may cause the visual occurrence of a pathological event to be out of phase with a pathological ECG event. Correlation of these out of phase events becomes difficult because different pathologies of the heart cause different pathologies in the QRS wave, which due to an out of phase condition, may cause misdiagnosis of the condition.

Another article on ECG QRS wave filtering is "R-Wave Detection in the Presence of Muscle Artifacts" by De Vel, IEEE Transactions on Biomedical Engineering, Vol. BME-31, No. 11, November 1984, pages 715-717. This discloses a filter and filtering for noises similar to those discussed in the Thakor article. In particular, the article deals with motion and muscle caused artifacts as well as other electrical perturbations. The disclosed filter, however, exhibits a 300 ms delay as shown in FIG. 3a thereof. This delay is not acceptable in an NMR imaging system for the reasons given above. Neither article recognizes the need for a filter in an NMR imaging system nor the nature of the noises created by such a system on the QRS signal. For example, the bandwidth of the Bo field induced noises relative to the QRS signal is not disclosed, nor more importantly, the need for time correlation of the NMR produced image with the ECG produced QRS wave.

SUMMARY OF THE INVENTION

A QRS signal filter according to the present invention is for use in real time with an NMR imaging system with negligible delay between the image and the filtered signal. The QRS signal has a given frequency range. A filter according to the present invention comprises a low pass filter for attenuating those portions of the QRS signal applied as an input and having a frequency above the given range to produce a first output signal. The low pass filter imposes a first given phase shift on the output signal relative to the input signal. A high pass filter responsive to the output signal applied as an input thereto attenuates those portions of the input signal applied thereto below the given range to produce a second output signal. The high pass filter imposes a second given phase shift relative to the time delay of the first output signal. The low and high pass filters are arranged so that the first and second phase shifts substantially cancel one another such that there is negligible time delay between the QRS signal applied to the low pass filter and the second output signal.

By way of example the low pass and high pass filters provide a bandwidth window of about 10 to 20 Hertz. The T-wave and the Bo field induced breathing artifact are typically below 10 Hertz and the noise signals introduced by the NMR system are typically around 100 Hertz providing relatively good filtering of the QRS signal.

In the Drawing:

FIG. 3 is a chart illustrating the response characteristics of a filter according to FIG. 2; and FIGS. 4a and 4b are waveforms produced by the filter of FIG. 2 respectively outside the magnetic field of FIG. 1 and inside the magnetic field (the time delays between the ECG wave and the filter output wave is due to a recording pen error).

DESCRIPTION OF THE PREFERRED EMBODIMENT

Figure 1:
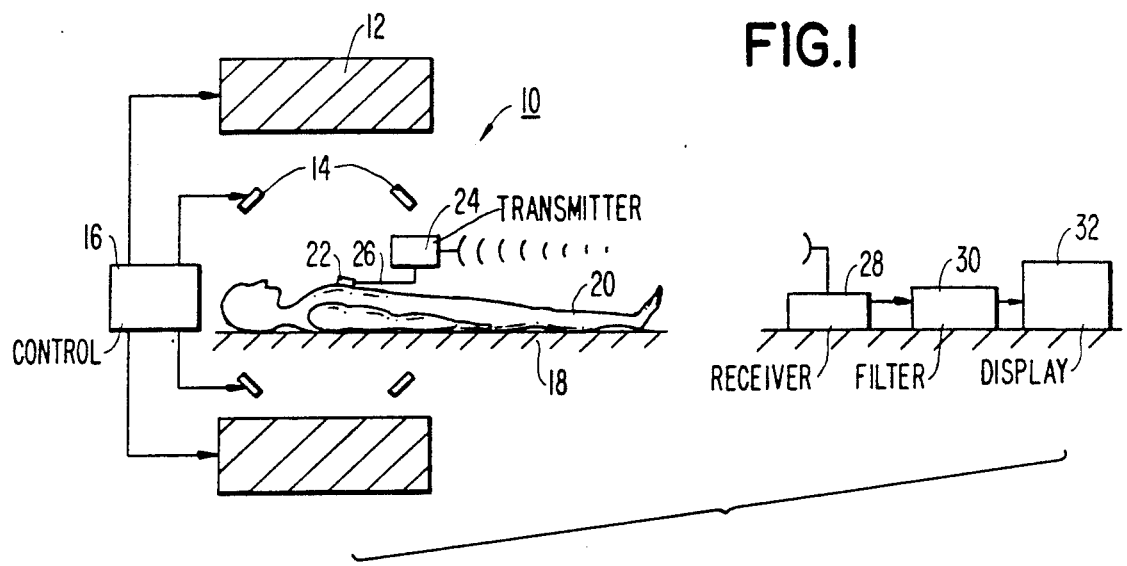
FIG. 1 is a side elevation view partially in section diagrammatically illustrating a system according to one embodiment of the present invention.

In FIG. 1, an NMR system 10 includes a main magnet 12 for producing a static magnetic field Bo. The NMR system, for example, may be a Philips S15-HP Gyroscan operating at 1.5 Telsa. A set of coils 14 provide radio frequency (rf) pulse induced fields. A control 16 operates the NMR system. Such systems are known and further details thereof need not be presented herein, the system being shown for purposes of illustration, the system also includes a patient table 18 for supporting a patient 20 being examined. In this example, the patient's heart is being imaged. It should be understood that the coils are shown for purposes of illustration and that coils specifically for imaging the heart may differ from what is shown.

Probes 22 (one being shown) are attached to the patient 20 for producing electrocardiogram (ECG)

signals. The signals produced by the probes are applied to a transmitter 24 via wires 26. The transmitter 24 may be Hewlett-Packard 78100A transmitter unit. The wires 26 lie on the patient's chest and move with the patient's breathing in the magnetic field inducing noise signals with the ECG signals. A receiver 28 outside the magnetic field of the system 10 receives the transmitted ECG signals. The received signals are applied to filter 30 of the present invention whose output is applied to display 32. Not shown are typical signal processing units for converting the received signals suitable for display on a monitor. The receiver 28 may be a Hewlett-Packard 78101A receiver. The display 32 may be Hewlett-Packard Model 78353B.

Figure 2:
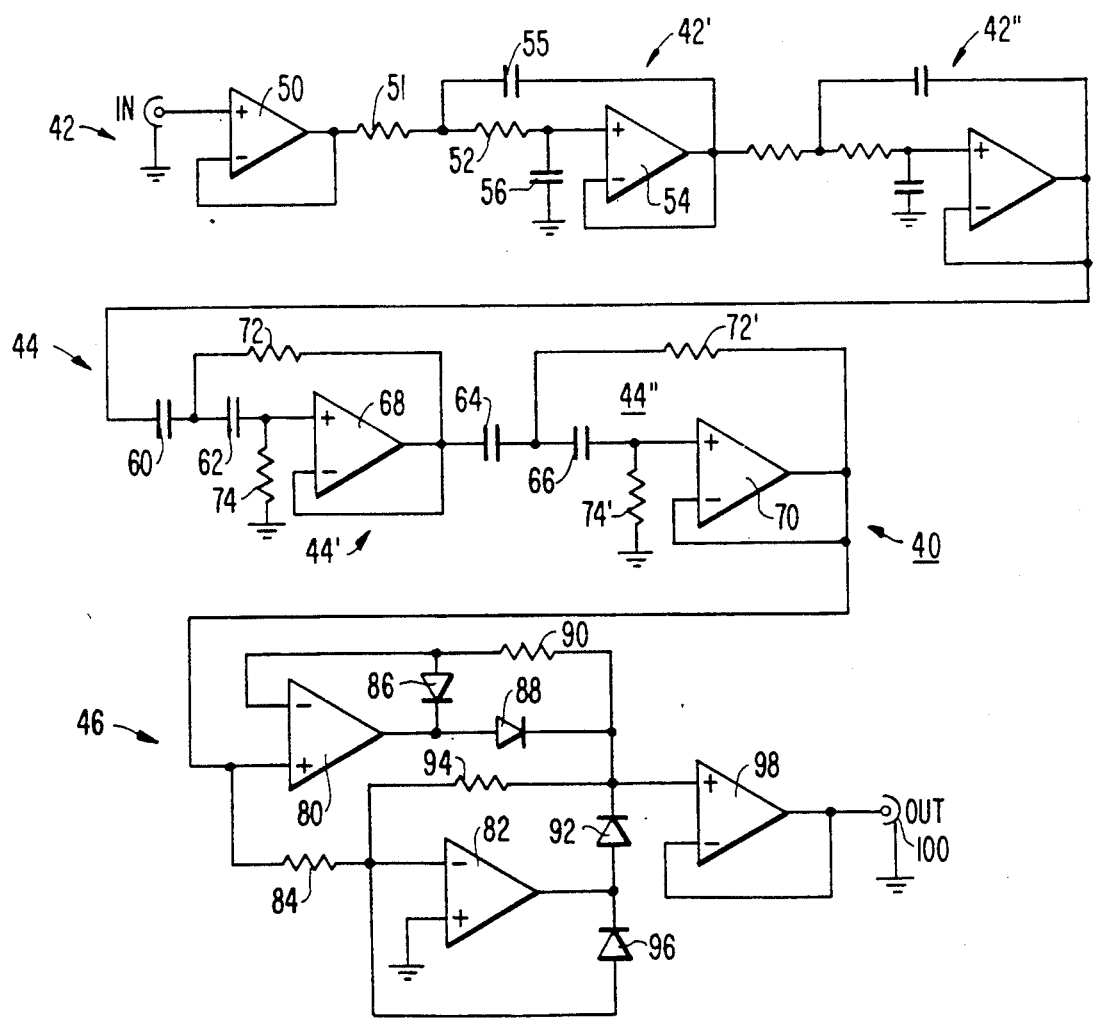
FIG. 2 is a schematic diagram of a filter according to one embodiment of the present invention for use in the system of FIG. 1.

In FIG. 2, filter 40 according to one embodiment of the present invention includes a low pass filter 42, a high pass filter 44 and an absolute value function filter 46 cascaded as shown. Filter 42 is a 4th order Butterworth unit having a −3 dB point at about 20 Hertz, 19.5 Hertz in this example. Filter 44 is a 4th order Butterworth unit having a −3 dB point at about 10 Hertz, 9.5 Hertz in this example. The absolute value filter is a precision full wave rectifier used to partially correct phase distortion in the reject band so that all frequency components of the R-wave would correctly add up.

Fourth order filters are used to provide a narrow bandwidth with relatively steep slopes. In FIG. 3, for example, the resultant curve shown by the dotted points has a slope at the −3 dB points of about −24 dB/octave. This slope is important because it insures that the unwanted low and high frequency noise components are attenuated from the QRS signal. The high frequency components, particularly those at 100 Hz, are introduced by the gradient pulses during NMR imaging. It is these noise signals which need to be removed by the low pass filter. Such noise signals typically are not present in signals to be filtered by prior art filters which therefore do not have as sharp a cut off at about 20 Hz. In contrast, the high pass filter cuts off low frequency noises, such as the T-wave which typically occurs at about 4 Hz. The 10 Hz window of the filter 40 provides good filtering for the QRS wave.

In FIG. 2, the low pass filter 42 comprises a buffer operational amplifier whose non-inverting input receives the signal to be filtered. The output of amplifier 50 is applied to a first low pass filter segment 42' via the non-inverting input of operational amplifier 54 via series connected resistances 51 and 52. A feedback capacitor 55 is connected between the amplifier 54 output and the junction of resistances 51 and 52. A second capacitor 56 couples the non-inverting input of the amplifier 54 to ground. The amplifier 54 output is also applied to its inverting input. A second filter segment 42" similar to segment 42' but having different capacitive and resistive component values than the components of segment 42' connects the output of segment 42' to the input of high pass filter 44. Filter 44 comprises a pair of series connected segments 44' and 44". Segments 44' and 44" are similarly arranged but also have different component values. Further, the capacitors and resistors of segments 44' and 44" are reversed in position relative to the resistors and capacitors of segments 42' and 42" over that capacitors 60 and 62 of segment 44' and capacitors 64 and 66 of segment 44" are series connected to the non-inverting inputs of the respective amplifiers 68 and 70 and the resistors 72, 72' and 74, 74' are respectively coupled in feedback and to ground.

The use of series connected resistors 60, 62 and 64, 66 for respective segments 42' and 42" as compared to capacitors for segments 44' and 44" is important. The phase shift introduced by filter 42 is counteracted by the phase shift of the filter 44 such that at 15 hertz (as set by the values of the different components) there is no discernible time delay introduced in the QRS signal outputted by filter 44 as compared to the QRS signal inputted to filter 42. That is, the filter 44 produces a signal opposite in phase as compared to the signal produced by filter 42. At the center frequency of 15 Hz there is no discernible phase shift between the input and output signals and thus negligible time delay. However, at the 10 and 20 Hz regions of the signals the two signals will be 180 degrees out of phase. This out of phase condition is compensated by filter 46 which adds the negative portions of the output signal of filter 44 to the signal of filter 42. That is, full wave rectification corrects for the phase differences of the low and high pass filters. While some phase distortion may remain in the rectified signal, this is acceptable.

Filter 46 comprises an operational amplifier 80 whose non-inverting input is connected to the output of amplifier 70 and to the inverting input of amplifier 82 via resistance 84. The output of amplifier 80 is connected to its inverting input through diode 86 across which are series connected diode 88 and resistance 90. The output of amplifier 82 is connected to the junction of diode 88 and resistance 90 by diode 92 and to its inverting input via series connected diode 92 and resistance 94. The output of amplifier 82 is also connected to its inverting input via diode 96. The non-inverting input of amplifier 82 is connected to ground. The junction of the cathodes of diodes 88 and 92 and resistance 94 is connected to the non-inverting input of buffer amplifier 98 whose output is connected to output terminal 100.

The operational amplifiers may be each part of a OP-471 Quad op-amp integrated circuit which comprises four operational amplifiers having unity gain and low noise. The amplifiers 50 and 98 are voltage followers employed as buffers.

In FIG. 4a, curve b is an ECG signal generated by the ECG probes outside a magnetic field. Curve a is a plot of the filtered wave curve b. The time delay between the filtered and unfiltered waves is due to a plotting pen error. In practice this delay is about +/−10 ms. FIG. 4b shows in curve b the corrupted signal due to an ECG signal being generated within a magnetic field of a field strength of 1.5 Telsa. It is not uncommon for T-waves under these conditions to exceed the amplitude of the R-wave. Curve a shows the filtered signal employing the filter of FIG. 2. Observe that the curves a of FIGS. 4a and 4b are similar regardless the wide disparities in the curves b. Curves a show the filtered QRS complex and a flat baseline. The Gyroscan is a unit which triggers in response to the peaks of the filtered signal applied thereto for generating the desired images. Therefore, it is important that when the Gyroscan is triggered the image being taken is occurring in real time coincidence with the triggering ECG signal. Otherwise, if the time difference is excessive, the scan will occur after the event causing the ECG QRS complex to occur. The Gyroscan reliably triggers on the filtered ECG on a routine basis. Pulsed static field gradient noise (not shown) is also routinely absent from the filtered ECG signal. The ECG filter provides relatively quick patient setup because triggering performance is unrelated to the ECG lead placement.

What is claimed is:

1. A QRS signal filter for use in real time with an NMR imaging system with negligible delay between the image and the filtered signal, said QRS signal having a given frequency range, said filter comprising:
   a low pass filter for attenuating those portions of the QRS signal applied as an input and having a frequency above said given range to produce a first output signal, said low pass filter including means for imposing a first given phase shift on said output signal relative to said input signal; and
   a high pass filter responsive to said output signal applied as an input thereto for attenuating those portions of an input signal applied thereto below said given range to produce a second output signal, said high pass filter including means for imposing a second given phase shift relative to the phase shift of the first output signal, said low and high pass filters being arranged so that said first and second phase shifts substantially cancel one another such that there is negligible time delay between said QRS signal applied to the low pass filter and said second output signal.

2. The filter of claim 1 further including absolute value filter means for processing said second output signal to correct for phase distortion in the second output signal.

3. The filter of claim 2 wherein the phase shift of the low pass filter is positive and the phase shift of the high pass filter is negative with the degree of said positive and negative shifts being about the same value.

4. The filter of claim 1 wherein said high and low pass filters are each fourth order Butterworth filters.

5. The filter of claim 1 including first and second operational amplifiers wherein the low pass filter comprises a pair of series connected input resistances connected to the input of the first operational amplifier and capacitive feedback means across said first operational amplifier and one of said input resistances and the high pass filter comprises a pair of series connected input capacitors connected to the input of the second operational amplifier and resistive feedback means across the latter amplifier and one of said input capacitors.

6. The filter of claim 1 wherein phase differences may be present between said high and low pass filters, said QRS signal filter further including full wave rectifier means for rectifying said second signal for correcting for said phase differences.

7. The filter of claim 1 wherein said low and high pass filters each include means for producing an output signal having a response of $-24$ dB per octave.

8. The filter of claim 1 wherein the attenuation response of the low pass filter is no less than about $-3$ dB at least about 20 Hertz and the attenuation response of the high pass filter is no less than about $-3$ dB at most about 10 Hertz.

9. The filter of claim 1 wherein the maximum combined time delay of the low and high pass filters is about 10 ms.

10. A QRS signal filter for use in real time with an NMR imaging system with negligible delay between the image and the filtered signal, said QRS signal being produced in the magnetic field of said system and having a given frequency range, said filter comprising:
    a low pass filter responsive to said QRS signal applied as an input thereto and having about a $-3$ dB response at least about 20 Hertz and a response characteristic of about $-24$ dB per octave to produce a first output signal, said low pass filter including means for imposing a first given phase shift on said output signal relative to said input signal;
    a high pass filter responsive to said output signal applied as an input thereto to produce a second output signal, said high pass filter having about a $-3$ dB response at most about 10 Hertz and a response characteristic of about $-24$ dB per octave, said high pass filter including means for imposing a second given phase shift relative to the phase shift of the first output signal, said low and high pass filters being arranged so that said first and second phase shifts substantially cancel one another at a given frequency such that there is negligible time delay between said QRS signal applied to the low pass filter and said second output signal; and
    full wave rectifier means for rectifying said second output signal.

11. The filter of claim 10 wherein said high and low pass filters are each of the 4th order.

12. An NMR imaging system comprising:
    magnet means for exposing a patient to a magnetic field, said patient creating signals in response to said magnetic field;
    imaging means responsive to said patient signals for creating an image of a patient in said field; and
    transmit and receive means for creating a patient QRS signal of a given frequency range in said magnetic field and for transmitting the QRS signal to said receive means;
    said receive means including QRS signal filter means such that the image produced by said imaging means and said QRS signal are substantially in phase;
    said filter means comprising:
    a low pass filter for attenuating those portions of the QRS signal applied as an input and having a frequency above said given range to produce a first output signal, said low pass filter including means for imposing a first given phase shift on said output signal relative to said input signal; and
    a high pass filter responsive to said output signal applied as an input thereto for attenuating those portions of an input signal applied thereto below said given range to produce a second output signal, said high pass filter including means for imposing a second given phase shift relative to the phase shift of the first output signal, said low and high pass filters being arranged so that said first and second phase shifts substantially cancel one another such that there is negligible time delay between said QRS signal applied to the low pass filter and said second output signal.

13. The filter of claim 12 wherein said low pass filter has about a $-3$ dB response at least about 20 Hertz and a response characteristic of about $-24$ dB per octave and the high pass filter has about a $-3$ dB response at most about 10 Hertz and a response characteristic of about $-24$ dB per octave.

14. An NMR imaging system comprising:
    magnet means for exposing a patient to a magnetic field, said patient creating signals in response to said magnetic field;
    imaging means responsive to said patient signals for creating an image of a patient in said field; and
    transmit and receive means for creating a patient QRS signal of a given frequency range in said magnetic field and for transmitting the QRS signal to said receive means;

said receive means including QRS signal filter means for filtering the QRS signal such that the image produced by said imaging means and said QRS signal are substantially in phase wherein there is negligible time delay between said created image and said filtered QRS signal.

15. The system of claim 14 wherein said filter means comprises cascaded high and low pass filters arranged to provide respective phase shifts which substantially cancel one another to thereby provide said negligible time delay.

* * * * *